US011947647B1

(12) United States Patent
Smith-Kipnis

(10) Patent No.: US 11,947,647 B1
(45) Date of Patent: Apr. 2, 2024

(54) USER AUTHENTICATION VIA GALVANIC SKIN RESPONSE

(71) Applicant: Wells Fargo Bank, N.A., San Francisco, CA (US)

(72) Inventor: Adam Benjamin Smith-Kipnis, Seattle, WA (US)

(73) Assignee: WELLS FARGO BANK, N.A., San Francisco, CA (US)

(*) Notice: Subject to any disclaimer, the term of this patent is extended or adjusted under 35 U.S.C. 154(b) by 172 days.

(21) Appl. No.: 17/543,804

(22) Filed: Dec. 7, 2021

Related U.S. Application Data

(63) Continuation of application No. 17/114,990, filed on Dec. 8, 2020, now Pat. No. 11,227,040.

(51) Int. Cl.
*G06F 21/32* (2013.01)
*A61B 5/0533* (2021.01)

(52) U.S. Cl.
CPC .......... *G06F 21/32* (2013.01); *A61B 5/0533* (2013.01)

(58) Field of Classification Search
CPC ........ G06F 21/32; A61B 5/0533; A61B 5/117
See application file for complete search history.

(56) References Cited

U.S. PATENT DOCUMENTS

| | | | |
|---|---|---|---|
| 9,305,194 B2 | 4/2016 | Adrangi et al. | |
| 10,643,206 B2 | 5/2020 | Kendrick et al. | |
| 10,667,033 B2 | 5/2020 | Boesen et al. | |
| 2008/0092232 A1* | 4/2008 | Lu | G06F 21/32 726/20 |
| 2013/0142363 A1* | 6/2013 | Amento | H04R 25/554 381/151 |
| 2013/0198694 A1 | 8/2013 | Rahman et al. | |
| 2014/0009262 A1* | 1/2014 | Robertson | A61B 5/332 340/5.82 |
| 2014/0298450 A1* | 10/2014 | Lymberopoulos | G06F 21/32 726/19 |
| 2014/0303900 A1 | 10/2014 | Rahman et al. | |
| 2014/0306821 A1 | 10/2014 | Rahman et al. | |
| 2015/0135310 A1 | 5/2015 | Lee | |
| 2015/0161461 A1* | 6/2015 | McNulty | G06V 40/1388 382/116 |
| 2017/0024713 A1 | 1/2017 | May et al. | |
| 2017/0257698 A1* | 9/2017 | Boesen | G10L 17/00 |
| 2018/0225437 A1* | 8/2018 | Suh | A61B 5/117 |
| 2018/0239976 A1 | 8/2018 | Cornelius et al. | |
| 2019/0052661 A1 | 2/2019 | Anand | |
| 2019/0139050 A1 | 5/2019 | Maheshwari | |
| 2019/0358515 A1* | 11/2019 | Tran | H04L 9/3236 |

(Continued)

*Primary Examiner* — Benyam Haile
(74) *Attorney, Agent, or Firm* — Merchant & Gould P.C.

(57) ABSTRACT

A method of authenticating a user via a galvanic skin response on electric computing device is described. The method includes receiving a request for user authentication from a second electronic computing device. The electronic computing device measures a change in the galvanic skin response associated with the user, and the change in the galvanic skin response is indicative of the user creating a physical connection between the electronic computing device and the second electronic computing device. The electronic computing device compares the galvanic skin response to a threshold skin conductance level. When the comparison of the galvanic skin response indicates, an authentication confirmation is sent to the second electronic computing device.

18 Claims, 8 Drawing Sheets

(56) References Cited

U.S. PATENT DOCUMENTS

| | | | |
|---|---|---|---|
| 2021/0169417 A1* | 6/2021 | Burton | A61B 5/4857 |
| 2021/0333906 A1* | 10/2021 | Noh | G06F 21/32 |
| 2022/0005022 A1* | 1/2022 | Tu | G06Q 20/02 |
| 2022/0261468 A1* | 8/2022 | Lin | H04R 25/30 |

* cited by examiner

USER AUTHENTICATION VIA GALVANIC SKIN RESPONSE

BACKGROUND

Users often need to locate and present an apparatus to authenticate themselves. Sometimes a user cannot find the appropriate apparatus (e.g., an ID badge, a mobile device), or the user does not wish to have to pull the apparatus out of his or her pocket or bag. Without the appropriate apparatus, a user may not gain access to something he or she otherwise would be allowed to access.

Users may also need to provide authentication to process a financial transaction, such as presenting a credit card and/or entering a PIN associated with the card, or presenting a smart phone having payment abilities. Again, sometimes a user cannot find the appropriate device (e.g. the credit card or smart phone) or the user does not remember the PIN. Without the appropriate device, the user may not complete the financial transaction.

SUMMARY

Embodiments of the disclosure are directed to authenticating a user based on a change in a galvanic skin response as detected by a wearable device.

In a first aspect, a method of authenticating a user via a galvanic skin response on an electric computing device is described. The method includes receiving a request for a user authentication from a second electronic computing device. The electronic computing device measures a change in the galvanic skin response associated with the user, and the change in the galvanic skin response is indicative of the user creating a physical connection between the electronic computing device and the second electronic computing device. The electronic computing device compares the galvanic skin response to a threshold skin conductance level. When the comparison of the galvanic skin response indicates, an authentication confirmation is sent to the second electronic computing device.

In another aspect, an electronic computing device comprising at least one processor and a system memory is described. The system memory includes instructions, which, when executed by the processor, cause the electronic computing device to perform the following: receive a request for a user authentication from a second electronic computing device; and measure a change in the galvanic skin response associated with the user via a galvanic skin response sensor. The change in the galvanic skin response is indicative of the user creating a physical connection between the electronic computing device and the second electronic computing device. The system memory includes further instructions to: compare the galvanic skin response to a threshold skin conductance level; and, when the comparison of the galvanic skin response indicates, send an authentication confirmation to the second electronic computing device.

In yet another aspect, a method of authorizing a user via a galvanic skin response on an electronic computing device is described. The method includes the following steps. A low voltage electrical signal is transmitted from the electronic computing device to the user. A change in the low voltage electrical signal is received, and the change in the low voltage electrical signal indicates that the user is in physical contact with the sensor of a requesting device. The change in the low voltage electrical signal is measured. The electronic computing device determines if the change in the low voltage electrical signal is at or above a threshold conductance level. When the change in the electrical signal is at or above the threshold conductance level and authentication confirmation is sent to the requesting device. When the change in the low voltage electrical signal is below the threshold conductance level, a denial for authentication to the requesting device is sent.

The details of one or more techniques are set forth in the accompanying drawings and the description below. Other features, objects, and advantages of these techniques will be apparent from the description, drawings, and claims.

DESCRIPTION OF THE DRAWINGS

The following drawings are illustrative of particular embodiments of the present disclosure and therefore do not limit the scope of the present disclosure. The drawings are not to scale and are intended for use in conjunction with the explanations in the following detailed description. Embodiments of the present disclosure will hereinafter be described in conjunction with the appended drawings, wherein like numerals denote like elements.

DETAILED DESCRIPTION

Figure 1:
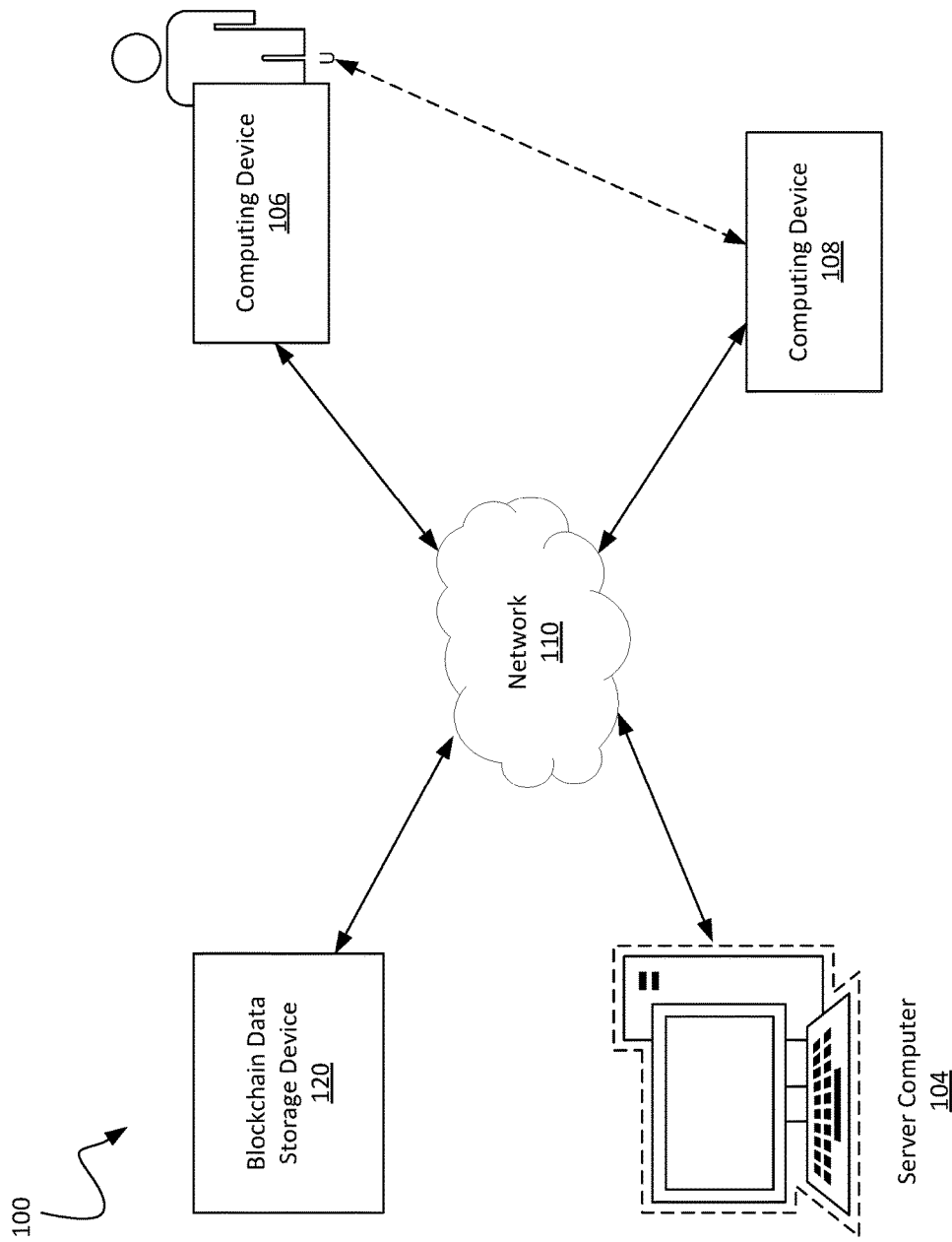
FIG. 1 illustrates an example environment that supports authentication of a user.

Various embodiments will be described in detail with reference to the drawings, wherein like reference numerals represent like parts and assemblies through the several views. Reference to various embodiments does not limit the scope of the claims attached hereto. Additionally, any examples set forth in this specification are not intended to be limiting and merely set forth the many possible embodiments for the appended claims.

Whenever appropriate, terms used in the singular also will include the plural and vice versa. The use of "a" herein means "one or more" unless stated otherwise or where the use of "one or more" is clearly inappropriate. The use of "or" means "and/or" unless stated otherwise. The use of "comprise," "comprises," "comprising," "include," "includes," and "including" are interchangeable and not intended to be limiting. The term "such as" also is not intended to be limiting. For example, the term "including" shall mean "including, but not limited to."

Electrodermal activity, specifically a galvanic skin response, refers to changes in sweat gland activity, which are measurable based on a change in electrical conduction. Changes in emotional arousal, in response to the user's environment, results in an increase of sweat gland activity, which produces the measurable electrical signal. Measuring the galvanic skin response can be used to measure the intensity of the user's response.

Sweat glands are present throughout the body, and the resultant change in electrical conductivity can be measured with a sensor. The density of sweat glands is highest in the hands and feet; therefore, a wearable device, such as a smart watch, is a good way to measure such change.

Measuring the change in electrical response can include measuring whether the response exceeds a threshold, for example, measuring a binary change. Measuring the change can also include measuring the amplitude and frequency of the electrical signal. In yet another example, measuring the change includes measuring a change in resistance of the electrical signal.

Skin conductance can be used for device-to-device communication. In a first example, skin conductance can be used for authenticating a user at an access terminal via a signal provided through the user's skin from a wearable device in lieu of, or in addition to, an access badge. In another example, skin conductance for device-to-device communication can transmit payment information via a signal provided through the user's skin from a wearable device to a payment terminal.

In yet another example, a financial transaction can be triggered based on skin contact between at least two users. Each user of the transaction is wearing a wearable device that can measure his or her skin conductance. When the skin of the payor and the skin of the payee touch, an electrical signal is enabled to be transferred from the wearable device of the payor to the wearable device of the payee to create a completed circuit.

FIG. 1 illustrates an example environment 100 that includes a first electronic computing device 106, a second electronic computing device 108, a server computer 104, an optional blockchain data storage device 120, and a network 110.

The environment generally supports the use of the electronic computing device 106, such as a wearable device, in measuring a galvanic skin response when a user U of the electronic computing device 106 is in physical contact with both the first electronic computing device 106 and the second electronic computing device 108.

The first electronic computing device 106 and/or the second electronic computing device 108 may be any of a wide range of electronic computing devices, including wearable devices. The second electronic computing device 108 may also be a computing device of secured terminal or a point-of-sale terminal.

A wearable device may comprise any of a wide range of computing devices that are configured to be attached to some portion of a user's body such that a signal transmitter and response sensor is in contact with the user's body. In some examples, the wearable device may comprise a computing device in the form of a watch, a bracelet, an arm band, an ankle band, an ear cuff, or another form factor capable of being worn by encircling some portion of the user's body. In other examples, the wearable device may comprise electronic skin technology, also referred to as "skin tech" or "digital tattoo," in the form of a thin, flexible film that includes embedded electronics capable of being worn by adhering directly to a user's skin, e.g., as a sticker, patch, or temporary tattoo. In some cases, electronics of the wearable device may include simple circuitry capable of responding to signals from the user's body, and/or responding to signals from an external computing device, for example, a computing device.

In a further example, the wearable device may be configured to operate as an accessory that is paired or linked to the electronic computing device 106. The wearable device may be considered a "dumb" device that does not have full communication and/or processing capabilities. For example, the wearable device may be used to produce and monitor a low voltage electrical signal, but send the monitored information to the electronic computing device 106 for further analysis. For example, the electronic computing device 106 may be configured to communicate with the second electronic computing device 108 in order response to a change in the low voltage electronic signal as received by the wearable device.

A low voltage electrical signal may be about 0.1-1.0 volts. In an example, the low voltage electrical signal provided may be about 0.2-0.7 volts. In yet another example, the low voltage electrical signal provided may be about 0.5-0.6 volts.

Another type of wearable device is a headset. A headset can include a wearable computer, a camera, and an optical display. The headset includes a wireless telecommunication capability, permitting a wireless connection between the wearable computing device and one or more server computers. The headset also includes voice recognition capability, permitting the user to direct the wearable computer via voice commands. In addition, in some implementations, the headset also includes biometric capability such as facial recognition, retinal scan capability, fingerprint, and voice print capability.

The first electronic computing device 106 is capable of communicating with the network 110 and communicating at least with the second electronic computing device 108. The first electronic computing device 106 is also capable of communicating with the server computer 104 and the optional blockchain data storage device 120.

The example network 110 is a computer network and can be any type of wireless network, wired network, and cellular network, including the Internet. The first electronic computing device 106 and/or the second electronic computing device 108 can communicate with the server computer 104 and/or the optional blockchain data storage device 120 via the network 110.

In an example, the example server computer 104 is an electronic computing device of a financial institution, such as a bank, when a financial transaction is occurring. In such an example, the server computer 104 houses and controls the banking aspects of a system when needed. For example, the server computer 104 receives a request for a financial transaction via the network 110 and processes the request. The request can be from one of the first electronic computing device 106 or second electronic computing device 108. The server computer 104 can process the request by, for example, transferring a monetary amount from a first account to a second account.

In another embodiment, the server computer 104 can be, for example, a physical server, or a virtual server hosted in a cloud storage environment. In some embodiments, the first electronic computing device 106 is capable of communicating with the server computer 104 and/or the second electronic computing device 108. Such communication can optionally occur via one or more wireless communication protocols, e.g., Wi-Fi (IEEE 802.11), short-range wireless communication to a Wi-Fi bridge, or other connection mechanism.

In an embodiment for processing a financial transaction, the server computer 104 can process the request, and a notification can be sent to the blockchain data storage device 120 via the network 110, where the transaction is memorialized. A notification of the transaction can also be sent via the network 110 to one of the first electronic computing device 106 or second electronic computing device 108, where the user can be notified of the completed transaction.

A blockchain data storage device 120 can be an electronic computing device or a plurality of electronic computing devices. The blockchain data storage device 120 can comprise a plurality of distributed, peer-to-peer storage devices, for example server computing devices, that can store the transaction data. The example blockchain data storage device 120 is a digital ledger that stores transactional data. The blockchain data storage device 120 can receive blockchain entries, or blocks, and store the associated data. The blockchain data storage device 120 can determine whether to store the data in a new block. There are examples described below and the blockchain can include hundreds or thousands of entries associated with transactions.

Figure 2:
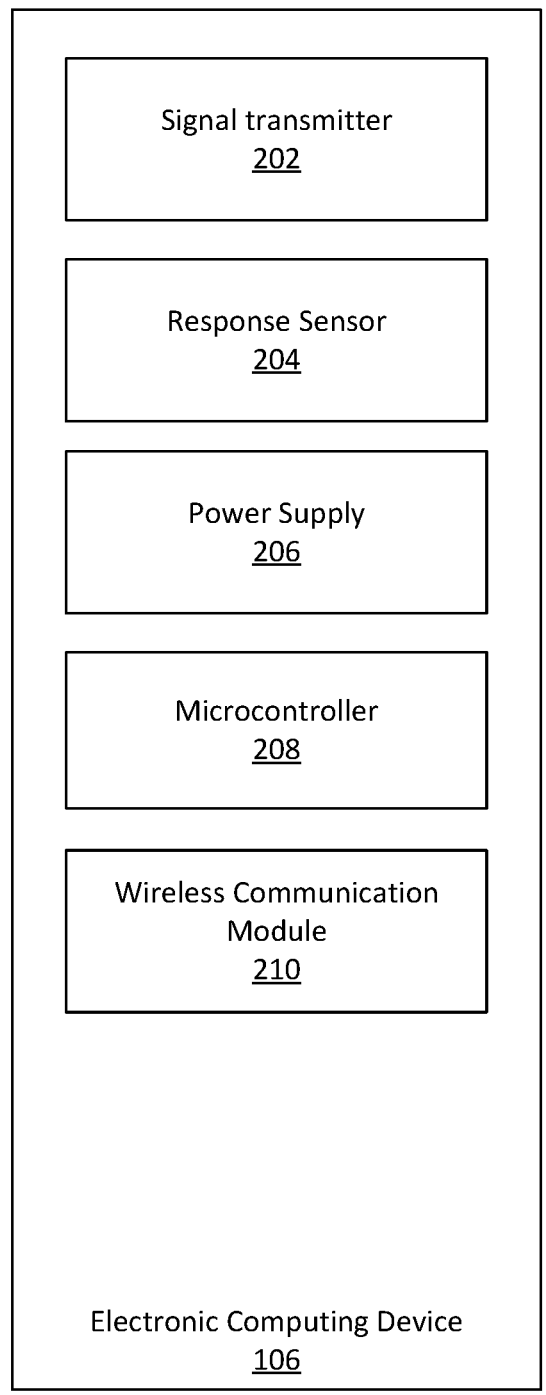
FIG. 2 illustrates a block diagram of components of an electronic computing device of the environment of FIG. 1.

FIG. 2 illustrates a block diagram of components of the electronic computing device 106, which includes a signal transmitter 202, a response sensor 204, a power supply 206, a microcontroller 208, and a wireless communication module 210.

The signal transmitter 202 is configured to produce a low voltage electrical signal and transmit it to the user via a physical contact. For example, when the electronic computing device 106 is a wearable smart watch, a physical contact point may be on the user's wrist. The signal transmitter 202 is located at a point on the watch to be in contact with the user's wrist. In a first example, the signal transmitter 202 may be constantly producing a low voltage electrical signal.

In an alternative example, a microcontroller 208 (described below) may determine when the signal transmitter 202 produces the low voltage electrical signal. The microcontroller 208 may receive a notification that the electronic computing device 106 is in proximity to a second electronic computing device 108, and at that point, the signal transmitter 202 produces the low voltage electrical signal.

A response sensor 204 measures a change in skin conductance. The change in skin conductance is what is referred to as the galvanic skin response. The response sensor 204 is configured to receive an electrical signal and measure the electrical signal. The response sensor 204, in conjunction with the microcontroller 208, determines the amplitude and frequency of the electrical signal, the resistance of the electrical signal, and/or whether or not an electrical signal is received.

The response sensor 204 may be a readily available sensor capable of measuring a change in electrical signaling. An example response sensor 204 useful in the applications described herein may include skin response sensors produced by Seeed Technology Co., Ltd., or LeuLog® GSR Sensor produced by Carolina®. However, other skin response sensors may be utilized.

The electrical signal response is used to determine whether or not a circuit is complete, which indicates that the user is in contact with both the electronic computing device 106 and a second electronic computing device 108 (also referred to herein as a "requesting device").

The power supply 206 provides power to the electronic computing device 106, including the signal transmitter 202 and the response sensor 204. The power supply 206 is a standard battery in the first electronic computing device 106.

The microcontroller 208 controls when the signal transmitter 202 produces a low voltage electrical signal. The microcontroller 208 is also configured to determine when the response sensor 204 receives a measurable electrical signal, and to determine whether or not the received electrical signal is at or above a threshold level. As described in more detail below, when the received electrical signal is at or above a threshold level, the user is in physical contact with the second electronic computing device 108 and the user authentication can occur.

A threshold level may be a percentage of the current provided of the low voltage electrical signal provided by the signal transmitter 202. For example, the threshold level may be 75% of the low voltage electrical signal provided. In another example, threshold level may be 50% of the low voltage electrical signal provided. In yet another example, threshold level may be 25% of the low voltage electrical signal provided.

In another example, a threshold level may also measure a binary change. When any electrical signal is detected, the threshold level is determined to be exceeded.

In yet another example, the threshold level corresponds to value of the amplitude and frequency of the measured electrical signal.

The wireless communication module 210 is configured to communicate with the second electronic computing device 108, the network 110, and/or the server computer 104. The wireless communication module 210 can include one or more wireless interfaces, such as a Wi-Fi interface and a Bluetooth interface. Interfaces for other types of wireless communication can be used in addition to or instead of Wi-Fi and Bluetooth. Other RF circuits can be included as well. In the example shown, the interfaces are capable of communication using at least one wireless communication protocol. In some examples, the electronic computing device 106 can communicate with the second electronic computing device 108 via the Wi-Fi interface or the Bluetooth interface.

Of course, in alternative embodiments, other wireless protocols could be implemented as well, via one or more additional wireless interfaces. In some examples, the electronic computing device 106 can wirelessly communicate with the second electronic computing device 108 through a desired wireless communications protocol. In some examples, the electronic computing device 106 can wirelessly control the operation of a secured access device, such as a locked door. The second electronic computing device 108 (the lock) of the door can utilize wireless protocols including, but not limited to, the IEEE 802.11 standard (Wi-Fi), the IEEE 802.15.4 standard (Zigbee and Z-wave), the IEEE 802.15.1 standard (Bluetooth®), a cellular network, a wireless local area network, near-field communication protocol, and/or other network protocols.

Figure 3:
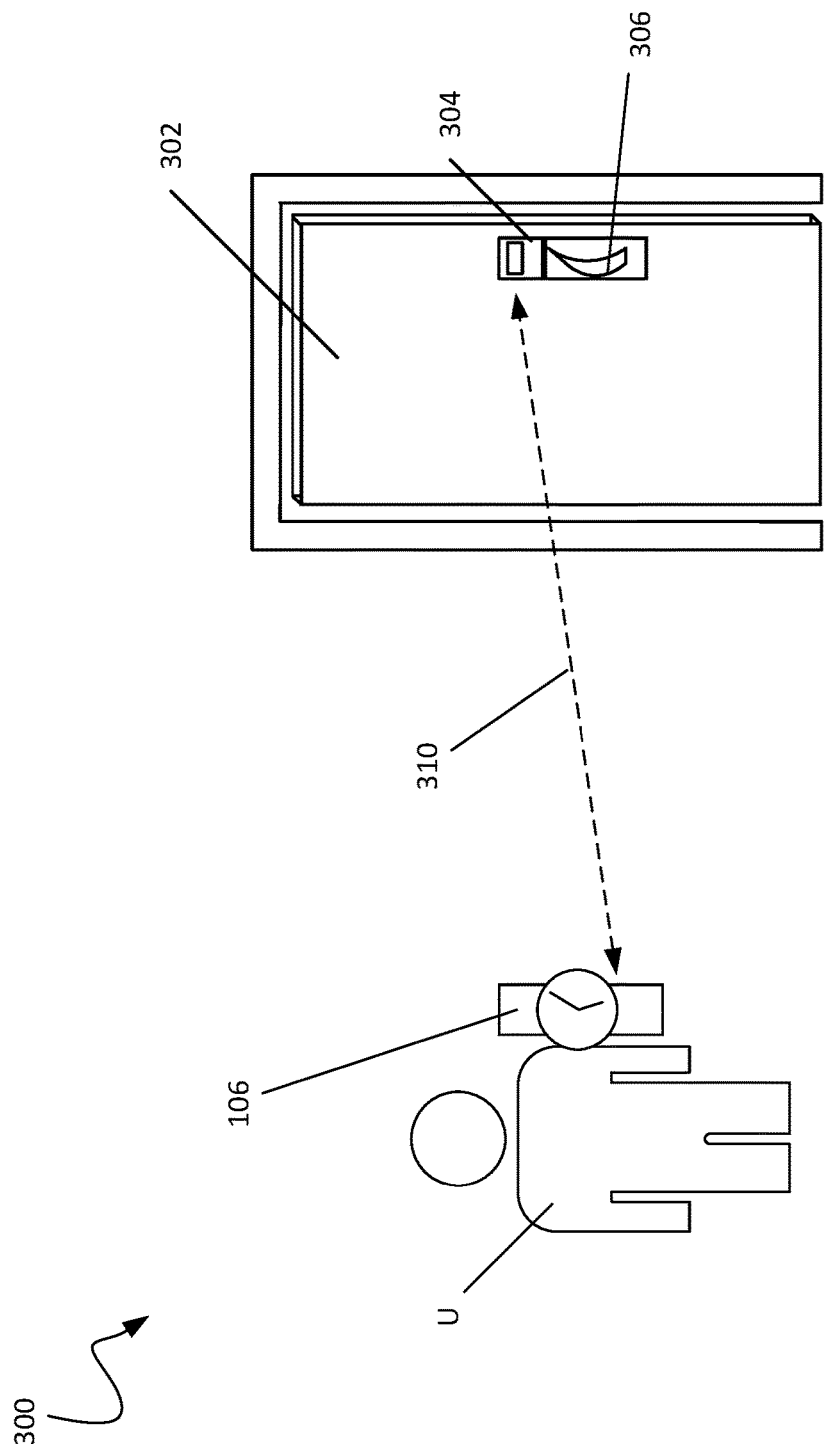
FIG. 3 illustrates an example use of the electronic computing device of FIG. 2.

FIG. 3 illustrates an example environment 300 of the user U of the electronic computing device 106 with a communication link 310 to a controlled access device 304. In the example shown, the controlled access device 304 is associated with a door 302. However, other points of access are contemplated.

The electronic computing device 106 may be used as a replacement for a key card, such as an ID badge or key fob. When the user U wants to be allowed access to the secured area, the user U, in conjunction with the electronic computing device 106, such as a wearable, touches some part of a second electronic computing device 108 to complete an electronic circuit, as described in more detail below.

The electronic computing device 106 produces the low voltage electrical signal via a physical touch with the user U. When the user U wants to be authenticated by the controlled access device 304 (the "second electronic computing device 108"), the user U physically touches the controlled access device 304 at a physical touch sensor 306. When the user U is in contact with both the response sensor 204 of the electronic computing device 106 and a physical touch sensor 306 of the controlled access device 304, a circuit is complete, and the electronic computing device 106 can measure an electronic signal.

When the electronic computing device 106 determines that the signal is above a threshold, the wireless communication module 210 can send a signal to the second electronic computing device 108 that the user is authenticated. In this example, the second electronic computing device 108 is the controlled access device 304, so the controlled access device 304 can allow the user U access to the door 302.

While a door 302 is used as the example controlled access device 304, other types of devices requiring user authentication are possible. For example, a controlled access device 304 may be a locked computing system, such as a computing system in a doctor's office, or a locked car.

In an example, the controlled access device 304 is a doorknob and the circuit is complete when the user U physically touches the doorknob with their hand to open the door. The electronic computing device 106 sends a specific voltage (as a constant voltage, an oscillation, or a pulse) to the user U. When the user U reaches out to the doorknob, the low voltage from the electronic computing device 106 is transmitted across the skin of the user to the physical touch sensor 306. Information is embedded in the electrical current and is exchanged between the electronic computing device 106 and the physical touch sensor 306 that facilitates an exchange of data or authentication.

Figure 4:
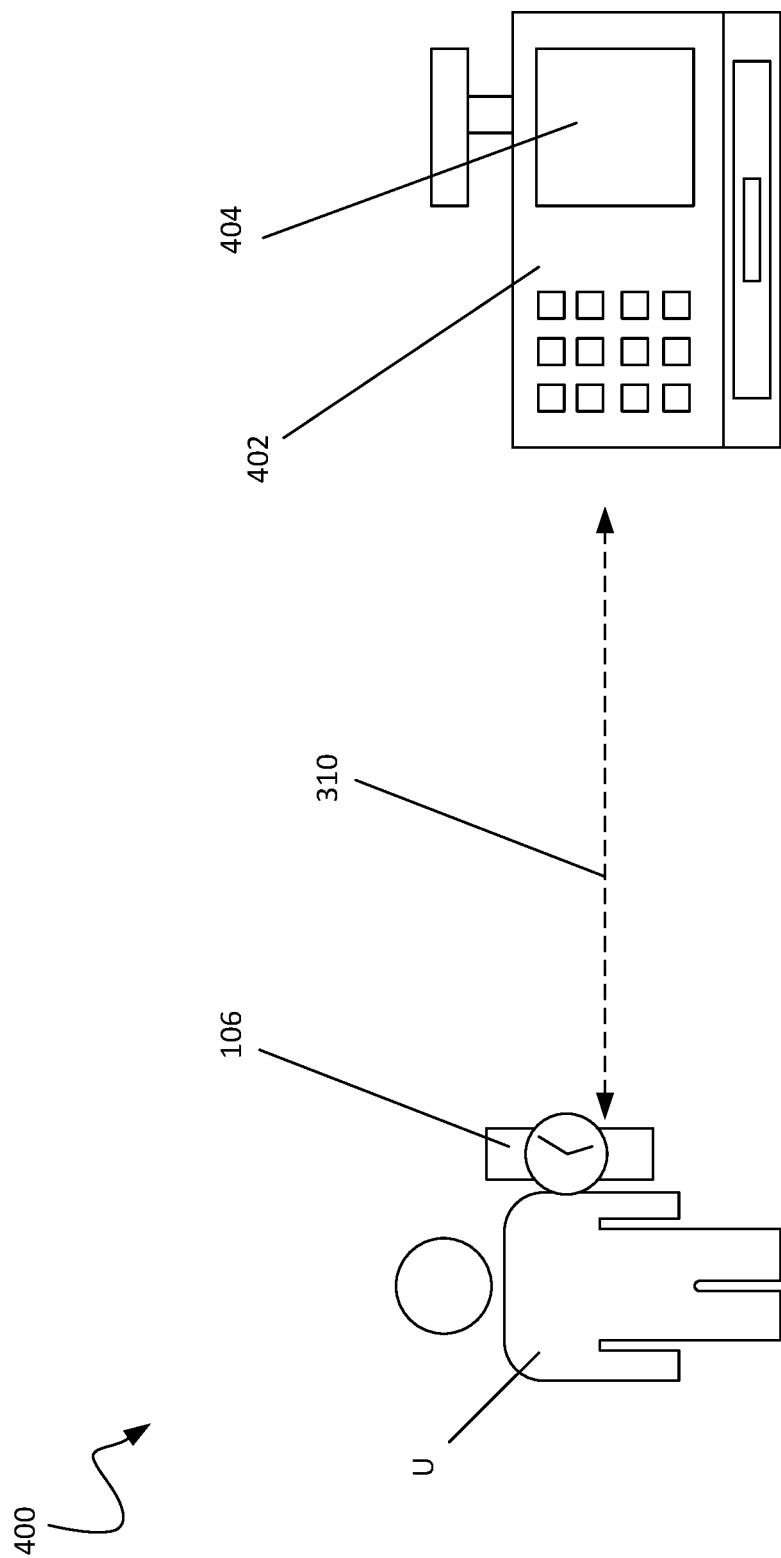
FIG. 4 illustrates another example use of the electronic computing device of FIG. 2.

FIG. 4 illustrates another example environment 400 of the user U with the electronic computing device 106 with the communication link 310 to a point-of-sale device 402. In the example environment 400 shown, the user U is making a purchase and the point-of-sale device 402 is requesting a payment authorization to complete the financial transaction.

The electronic computing device 106 may be used as a replacement for a credit card authorization or a signature required for transaction verification. However, these examples are not to be seen as limiting.

When the user U desires to authenticate a payment at the point-of-sale device 402, the user U, in conjunction with the electronic computing device 106, such as a wearable device, physically touches a touch sensor 404 of the point-of-sale device 402. The electronic computing device 106 produces the low voltage electrical signal via the physical touch with the user U. When the user U is in contact with both the electronic computing device 106 and the touch sensor 404 of the point-of-sale device 402, the circuit is complete and the electronic computing device 106 can measure an electrical signal.

When the electronic computing device 106 determines that the signal is above the threshold, the wireless communication module 210 can send a message to the point-of-sale device 402 that the user is authenticated and the purchase transaction is authorized. The point of sale device (also referred to as the "requesting device") can request a payment via the network 110 to the server computer 104; therefore, completing the purchase transaction.

If the change in electrical signal is below the threshold, the electronic computing device 106 can either not send an authentication communication or can send a message denying the authentication.

The financial transaction may be memorialized in a blockchain ledger managed and stored by the blockchain data storage device 120. For example, an example ledger is provided below. In this example, the blockchain is used to memorialize the financial transaction.

| Begin Blockchain |
| --- |
| User: User A |
| Beginning Amount: $100.00 |
| Entry: 100001 |
| Date: Aug. 30, 2020 |
| Galvanic Response: Received: Value 0.4 V |
| Transferred Amount: $30.00 |
| From: User A |
| To: Department Store |
| Beginning Amount: $130.00 |
| Ending Amount: $100.00 |
| End Blockchain |

In a similar embodiment, the electronic computing device 106 can communicate with a different electronic device. In an example, the electronic computing device 106 sends a specific voltage (as a constant voltage, an oscillation, or a pulse) to the user U. When the user U touches an electronic device, the low voltage from the electronic computing device 106 is transmitted across the skin of the user to a physical touch sensor 306 associated with the electronic device. In an example, the physical touch sensor 306 is located on a keyboard or a mouse associated with the electronic device. Information is embedded in the electrical current and is exchanged between the electronic computing device 106 and the physical touch sensor 306 that facilitates an exchange of data or authentication.

Figure 5:
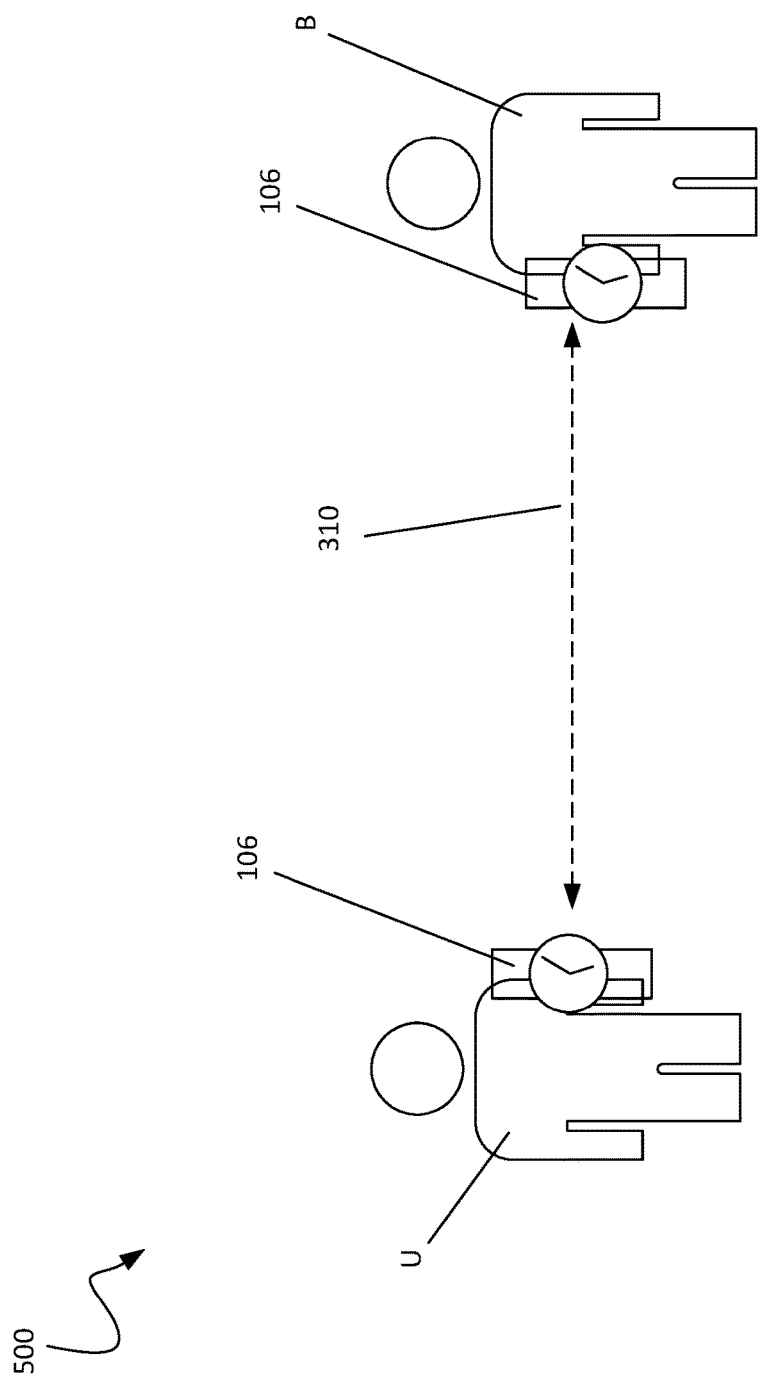
FIG. 5 illustrates another example use of the electronic computing device of FIG. 2.

FIG. 5 illustrates yet another example environment 500 of the user U with the electronic computing device 106 with the communication link 310 to the second electronic computing device 108 of a second user B. As shown in the example environment 500, the electronic computing device 106 is a smart watch and the second electronic computing device 108 is also a smart watch. In the example environment 500, the user B may be requesting a payment from the user U. When the user U wants to authenticate the payment or otherwise complete the transaction to the user B, the user U physically touches the user B.

In the example environment 500, each user U, B respectively, has the first and second electronic computing devices 106, 108 that is physically touching the respective user's skin. For example, a physical touch occurs when the user U and the user B shake hands. When the user U physically touches the user B, a circuit is completed. The electronic computing device 106 (and/or second electronic computing device 108) can then measure the presence of or the change in the electrical signal.

When the electronic computing device 106 determines that the signal is above the threshold level, the wireless communication module 210 can send a signal to the second electronic computing device 108 that the transaction should be processed.

In a further example, when a user U and user B desire to complete the transaction, the time at which the user U and user B are in physical contact with each other must be above a predetermined time period. Requiring that the users are in physical contact with each other for at least a predetermined time period ensures that incidental contact is not sufficient to complete a transaction.

A predetermined time period may be at least 1 second. For example, the predetermined time period may be from about 1 second to about 5 seconds. In another example, the predetermined time period may from about 2 seconds to about 3 seconds.

In a further example, the electronic computing device 106 may produce a notification that the response sensor 204 has received a measurable electrical signal. The notification may be a visual signal, such as a text notification on a user interface of the electronic computing device 106. The notification may also be an audible signal from the electronic computing device 106.

In another example, more than two users may be physically touching. For example, if multiple users need to pay for a shared meal at a restaurant, a chain of users create physical contact with each other to signal to the point-of-sale device 402 that the total bill amount should be split among the users in the chain.

Another example embodiment of using the electronic computing device 106 described herein is to track inventory. In an example, the user U is wearing the electronic computing device 106 that sends a specific voltage (as a constant voltage, an oscillation, or a pulse) to the user U. When the user U touches an inventory item (comprising a physical touch sensor 306) the low voltage from the electronic computing device 106 is transmitted across the skin of the user to the physical touch sensor 306. Information is embedded in the electrical current and is exchanged between the electronic computing device 106 and the physical touch sensor 306 that facilitates an exchange of data or authentication, which allows for the tracking of inventory.

In yet another example, a user U wearing an electronic computing device 106 is capable of communicating wirelessly with another electronic device. A user U may be subjected to a stimulus (visual, audible, tangible, or other similar stimulus) that produces a galvanic skin response. Once the user's specific response is determined, the specific measurement of the response can be used as a factor of authentication. For example, a user U is shown an image of a "pony" while at an ATM. The user's response to this image has been previously determined, so the user U can be authenticated at the ATM based on the response to the image of the pony.

Figure 6:
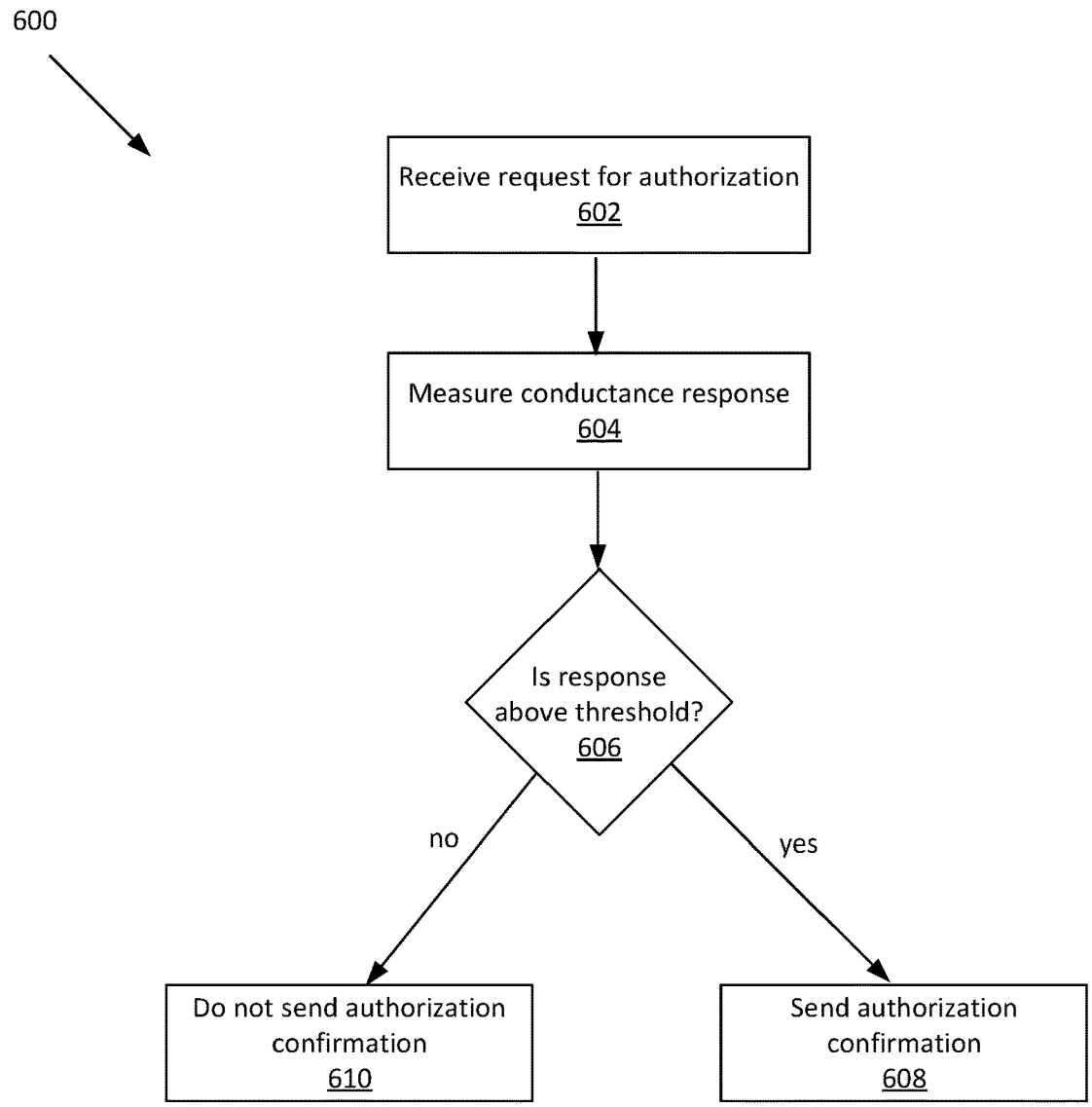
FIG. 6 illustrates an example block diagram of a method of use of the electronic computing device of FIG. 2.

FIG. 6 illustrates an example method 600 of determining when a user of the electronic computing device 106 is authenticated and sending authentication data associated with the authentication to the second electronic computing device 108.

At step 602, a request for authentication is received at the electronic computing device 106. The request may be received from a plurality of different second electronic computing devices 108, such as a door lock, a point-of-sale system, or a second wearable computing device.

At step 604, the electronic computing device 106 measures the conductive response, otherwise referred to as a change in detected electrical signaling, of the user U. Measuring the conductive response includes having the electronic computing device 106 send the low voltage electrical signal to the user U and measuring whether or not the electrical signal response changes.

The response or change in electrical signaling can be measured by sensing a change in amplitude and/or frequency of the electrical signal, a change in resistance of the electrical signal, or a change in a binary signal. The conductive response changes when the user is in contact with another electronic computing device, which causes a completed circuit and a change in electrical signaling.

At step 606, it is determined whether the electrical signaling response is above a predetermined threshold. The predetermined threshold is a level above a baseline response, at which it is more than likely that the circuit between the first electronic computing device 106 and the second electronic computing device 108 is creating a purposeful circuit.

As described above, the threshold level is a percentage of the current of the low voltage electrical signal provided by the signal transmitter 202.

If the response is not above the threshold, the method 600 moves to step 610. At step 610, an authentication confirmation is not sent to the second electronic computing device 108. In the first embodiment, no message is sent to the second electronic computing device 108. In another embodiment, a denial of authentication communication is sent.

If the response is above the threshold, the method 600 moves to step 608. At step 608, an authentication confirmation is sent from the electronic computing device 106 to the second electronic computing device 108.

Figure 7:
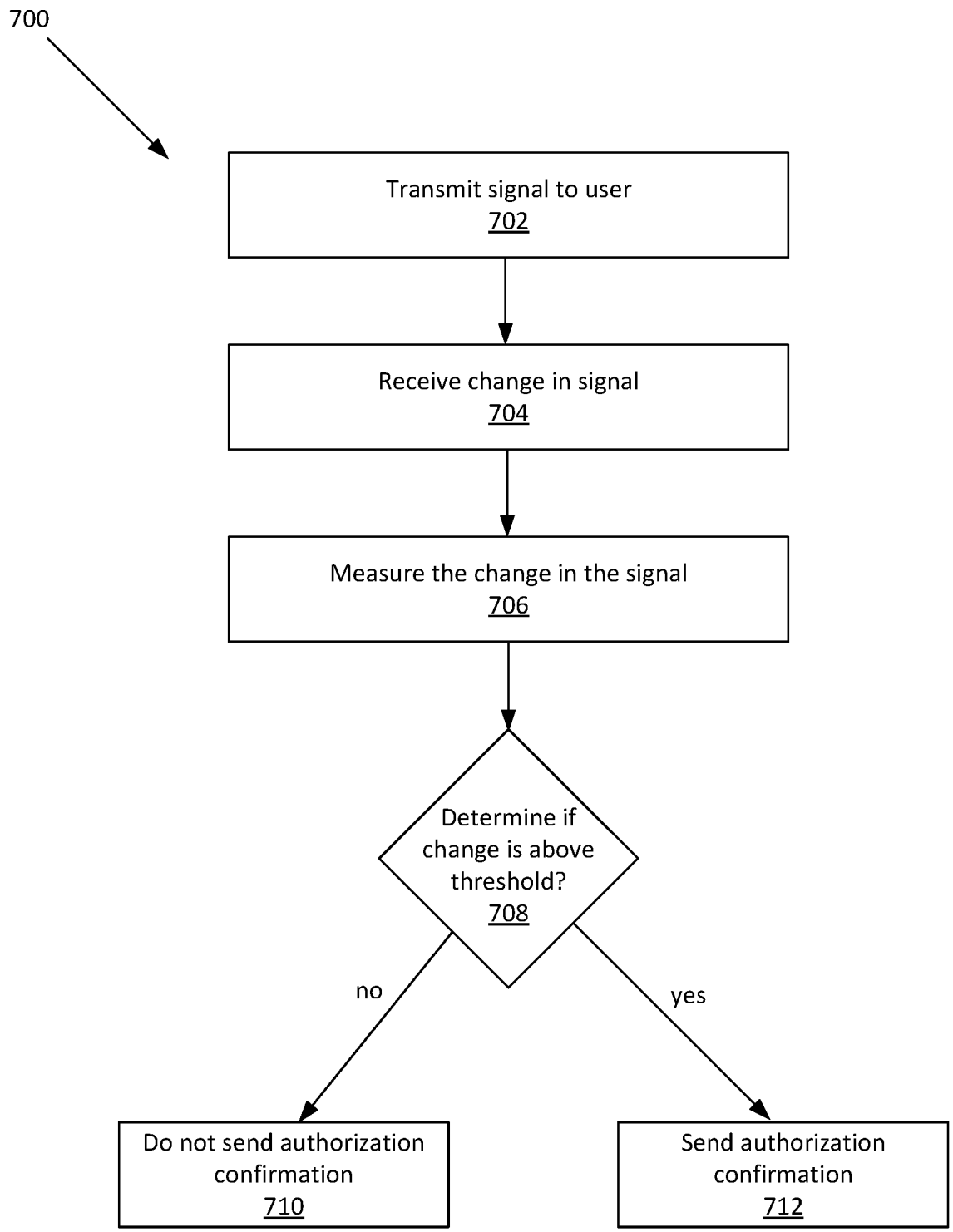
FIG. 7 illustrates another example block diagram of a method of use of the electronic computing device of FIG. 2

FIG. 7 illustrates the example method 700 of determining when the first electronic computing device 106 is authenticated based on a galvanic skin response of the user U.

At step 702, the low voltage electrical signal is transmitted to the user U by the electronic computing device 106. The low voltage electrical signal can be detectable by the response sensor 204 when the user U is in physical contact with the requesting device, such as the second electronic computing device 108. The second electronic computing device 108 also has a physical touch sensor.

In a first example embodiment, the electronic computing device 106 constantly emits the low voltage electrical signal to the user U. In another example embodiment, the electronic computing device 106 emits the low voltage electrical signal upon proximate detection of the second electronic computing device 108.

At step 704, a change in the electrical signal is received. This can occur when the user U touches the physical touch sensor of the second electronic computing device 108 while also in physical contact with the electronic computing device 106. The change in electrical signal can be a change in amplitude and frequency of the electrical signal, a change in the resistance of the electrical signal, or a change in a binary response of the electrical signal.

At step 706, the value of the change of the electrical signal is measured. The value of the change of the electrical signal can be received by the response sensor 204 of the electronic computing device 106 and calculated by the microcontroller 208.

At step 708, it is determined whether the change of the electrical signal is above the predetermined threshold. The predetermined threshold is a level above a baseline response, at which it is more likely than not that the completed circuit between the first electronic computing device 106 and the second electronic computing device 108 is creating a purposeful circuit. In other words, the predetermined threshold is high enough to ensure that incidental contact between the user U and the second electronic computing device 108 does not trigger an authentication communication. As described above, the threshold level is a percentage of the current of the low voltage electrical signal provided by the signal transmitter 202.

If the response, or change in electrical signaling, is not above the predetermined threshold, the method 700 moves to step 710. At step 710, the authentication confirmation is not sent to the second electronic computing device 108. In the first embodiment, no message is sent to the second electronic computing device 108. In another embodiment, a denial of authentication communication is sent to the second electronic computing device 108.

If the response is above the threshold, the method 700 moves to step 712. At step 712, the authentication confirmation is sent from the electronic computing device 106 to the second electronic computing device 108.

Figure 8:
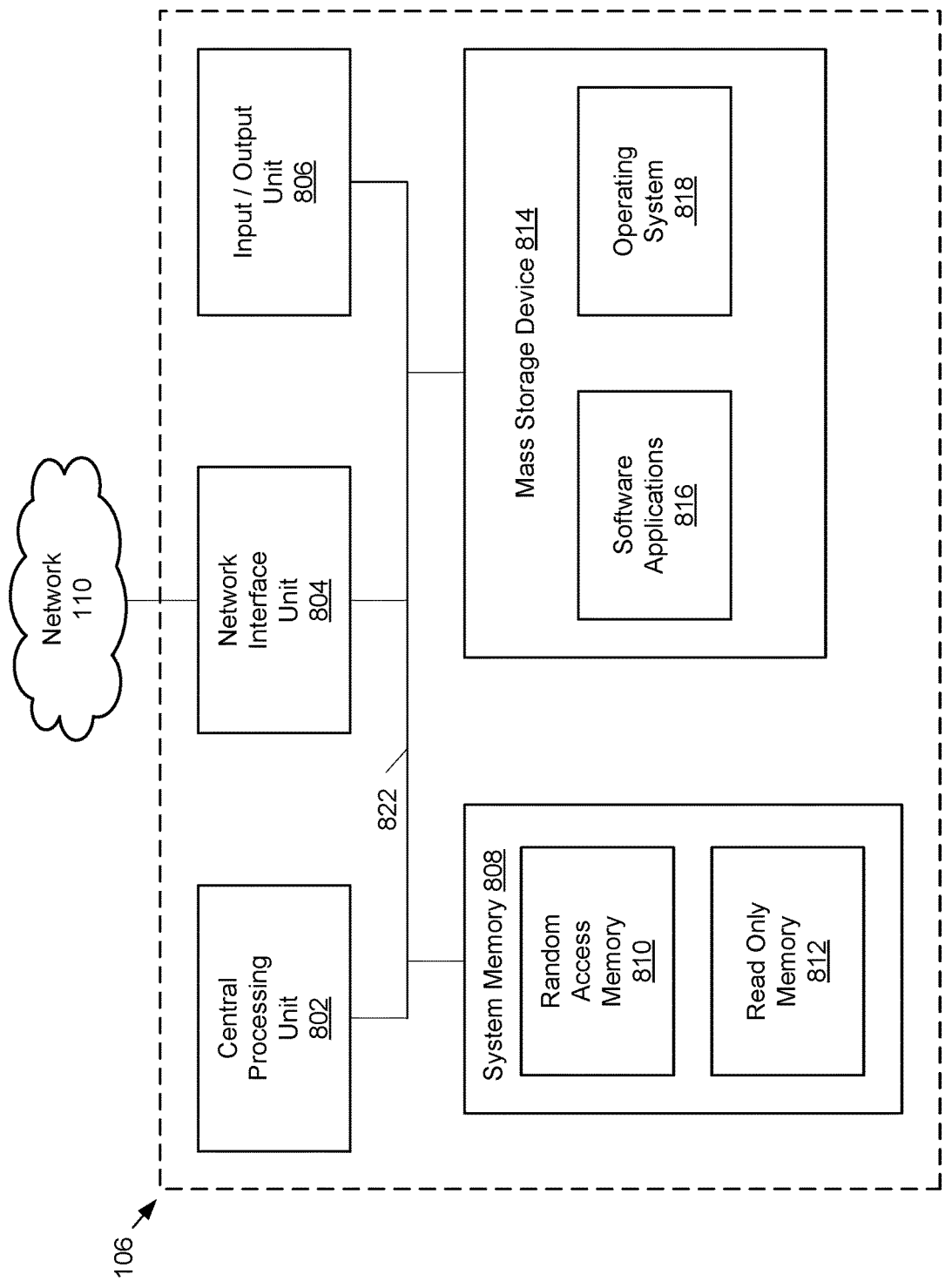
FIG. 8 illustrates an example block diagram of the electronic computing device of FIG. 1.

As illustrated in FIG. 8, example physical components of the electronic computing device 106 are shown. Other computing devices (e.g., the server computer 104, the second electronic computing device 108, and the blockchain data storage device 120) can be configured in a similar manner.

As illustrated in the example of FIG. 8, the example electronic computing device 106 includes at least one central processing unit ("CPU") 802, also referred to as a processor, a system memory 808, and a system bus 822 that couples the system memory 808 to the CPU 802. The system memory 808 includes a random access memory ("RAM") 810 and a read-only memory ("ROM") 812. A basic input/output system that contains the basic routines that help to transfer information between elements within the electronic computing device 106, such as during startup, is stored in the ROM 812. The electronic computing device 106 further includes a mass storage device 814. The mass storage device 814 is able to store software instructions and data. Some or all of the components of the electronic computing device 106 can also be included in the server computer 104 and any other computing devices described herein.

The mass storage device 814 is connected to the CPU 802 through a mass storage controller (not shown) connected to the system bus 822. The mass storage device 814 and its associated computer-readable data storage media provide non-volatile, non-transitory storage for the electronic computing device 106. Although the description of computer-readable data storage media contained herein refers to a mass storage device, such as a hard disk or solid state disk, it should be appreciated by those skilled in the art that computer-readable data storage media can be any available non-transitory, physical device or article of manufacture.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the electronic computing device 106.

According to various embodiments of the invention, the electronic computing device 106 may operate in a networked environment using logical connections to remote network devices through the network 110, such as a wireless network, the Internet, or another type of network. The electronic computing device 106 may connect to the network 820 through a network interface unit 804 connected to the system bus 822. It should be appreciated that the network interface unit 804 may also be utilized to connect to other types of networks and remote computing systems. The electronic computing device 106 also includes an input/output controller 806 for receiving and processing input from a number of other devices, including a touch user interface display screen, or another type of input device. Similarly, the input/output controller 806 may provide output to a touch user interface display screen or other type of output device.

As mentioned briefly above, the mass storage device 814 and the RAM 810 of the electronic computing device 106 can store software instructions and data. The software instructions include an operating system 818 suitable for controlling the operation of the electronic computing device 106. The mass storage device 814 and/or the RAM 810 also stores software instructions and software applications 816, that when executed by the CPU 802, cause the electronic computing device 106 to provide the functionality of the electronic computing device 106 discussed in this document. For example, the mass storage device 814 and/or the RAM 810 can store software instructions that, when executed by the CPU 802, cause the electronic computing device 106 to display received data on the display screen of the electronic computing device 106.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. A method of authenticating a financial transaction, the method comprising:
   receiving a payment request for the financial transaction from a payment terminal;
   measuring a galvanic skin response of a user;
   authorizing the payment request by authenticating using the galvanic skin response of the user, the galvanic skin response indicating that the user has created a physical connection between two electronic computing devices, with one of the two electronic computing devices being the payment terminal; and
   storing details of the financial transaction in a blockchain.

2. The method of claim 1, further comprising transmitting a low voltage electrical signal through the user to measure the galvanic skin response.

3. The method of claim 1, wherein measuring the galvanic skin response comprises measuring an amplitude and frequency of a conductance signal, and the galvanic skin response is at or above a threshold skin conductance level when the amplitude and frequency is higher than a baseline amplitude and frequency.

4. The method of claim 1, wherein measuring the galvanic skin response comprises measuring a resistance of a skin of the user, and the galvanic skin response is at or above a threshold skin conductance level when the resistance is higher than a baseline resistance.

5. The method of claim 1, wherein measuring the galvanic skin response comprises detecting the galvanic skin response using a wearable device.

6. The method of claim 1, wherein storing the details of the financial transaction in the blockchain further comprises storing the details of the financial transaction in a ledger of the blockchain.

7. The method of claim 6, further comprising storing a payment date, a galvanic response value, and a payment amount in the ledger of the blockchain.

8. The method of claim 1, wherein receiving the payment request for the financial transaction further comprises receiving the payment request at a point-of-sale device.

9. The method of claim 8, further comprising allowing the user to touch the point-of-sale device to measure the galvanic skin response.

10. An electronic computing device, comprising:
    a processor; and
    a system memory, the system memory including instructions which, when executed by the processor, cause the electronic computing device to:

receive a payment request for a financial transaction from a payment terminal;

measure a galvanic skin response of a user;

authorize the payment request by authenticating using the galvanic skin response of the user, the galvanic skin response indicating that the user has created a physical connection between two electronic computing devices, with one of the two electronic computing devices being the payment terminal; and store details of the financial transaction in a blockchain.

11. The electronic computing device of claim 10, comprising further instructions which, when executed by the processor, cause the electronic computing device to transmit a low voltage electrical signal through the user to measure the galvanic skin response.

12. The electronic computing device of claim 10, wherein to measure the galvanic skin response comprises to measure an amplitude and frequency of a conductance signal, and the galvanic skin response is at or above a threshold skin conductance level when the amplitude and frequency is higher than a baseline amplitude and frequency.

13. The electronic computing device of claim 10, wherein to measure the galvanic skin response comprises to measure a resistance of a skin of the user, and the galvanic skin response is at or above a threshold skin conductance level when the resistance is higher than a baseline resistance.

14. The electronic computing device of claim 10, wherein to measure the galvanic skin response comprises to detect the galvanic skin response using a wearable device.

15. The electronic computing device of claim 10, wherein to store the details of the financial transaction in the blockchain further comprises to store the details of the financial transaction in a ledger of the blockchain.

16. The electronic computing device of claim 15, comprising further instructions which, when executed by the processor, cause the electronic computing device to store a payment date, a galvanic response value, and a payment amount in the ledger of the blockchain.

17. The electronic computing device of claim 10, wherein to receive the payment request for the financial transaction further comprises to receive the payment request at a point-of-sale device.

18. The electronic computing device of claim 17, comprising further instructions which, when executed by the processor, cause the electronic computing device to allow the user to touch the point-of-sale device to measure the galvanic skin response.

* * * * *